United States Patent
Zoran et al.

(10) Patent No.: US 8,979,834 B2
(45) Date of Patent: Mar. 17, 2015

(54) LAPAROSCOPIC ELECTROSURGICAL ELECTRICAL LEAKAGE DETECTION

(75) Inventors: Arik Zoran, Clearwater, FL (US); Gregory A. Konesky, Hampton Bays, NY (US); Borislav S. Simeonov, St. Petersburg, FL (US); Jeffrey C. Rencher, Sarasota, FL (US)

(73) Assignee: Bovie Medical Corporation, Clearwater, FL (US)

( * ) Notice: Subject to any disclaimer, the term of this patent is extended or adjusted under 35 U.S.C. 154(b) by 410 days.

(21) Appl. No.: 13/555,220

(22) Filed: Jul. 23, 2012

(65) Prior Publication Data

US 2012/0330305 A1    Dec. 27, 2012

Related U.S. Application Data

(63) Continuation-in-part of application No. 13/355,729, filed on Jan. 23, 2012, now Pat. No. 8,226,640, which is a continuation of application No. 12/056,436, filed on Mar. 27, 2008, now Pat. No. 8,100,897.

(51) Int. Cl.
| | |
|---|---|
| A61B 18/04 | (2006.01) |
| A61B 18/14 | (2006.01) |
| A61B 18/12 | (2006.01) |
| A61B 18/00 | (2006.01) |

(52) U.S. Cl.
CPC ... *A61B 18/1233* (2013.01); *A61B 2018/00827* (2013.01); *A61B 2018/1286* (2013.01)
USPC .................. 606/34; 606/33; 606/41

(58) Field of Classification Search
USPC ............... 606/32–50; 607/101–102
See application file for complete search history.

(56) References Cited

U.S. PATENT DOCUMENTS

| | | |
|---|---|---|
| 3,683,923 A | 8/1972 | Anderson |
| 3,946,738 A | 3/1976 | Newton et al. |
| 4,094,320 A * | 6/1978 | Newton et al. .................. 606/35 |
| 4,200,105 A | 4/1980 | Gosner |
| 4,437,464 A | 3/1984 | Crow |
| 4,662,369 A | 5/1987 | Ensslin |
| 5,152,762 A | 10/1992 | McElhenney |

(Continued)

OTHER PUBLICATIONS

Ming-Ping Wu et al., "Complications and Recommended Practices for Electrosurgery in Laparoscopy", Am J Surg., Jan. 2000; 179:67-73.

(Continued)

*Primary Examiner* — Michael Peffley
*Assistant Examiner* — Khadijeh Vahdat
(74) *Attorney, Agent, or Firm* — Gerald E. Hespos; Michael J. Porco; Matthew T. Hespos

(57) ABSTRACT

An apparatus for use with an endoscopic applicator. The apparatus including a support member configured to be removably coupled to a shaft of the applicator; a first sensor disposed on the distal end of the support member and for outputting a first signal indicative of current measured at the distal end of an active electrode supported in the shaft; and a second sensor disposed on the proximal end of the support member and for outputting a second signal indicative of current measured at the proximal end of the active electrode, wherein a difference value of the first and second signal is indicative of leakage of current within the shaft. In one embodiment, the first and second sensors are magnetic sensors for contactlessly sensing parameters of the active electrode.

23 Claims, 10 Drawing Sheets

(56) References Cited

U.S. PATENT DOCUMENTS

| | | |
|---|---|---|
| 5,312,401 A | 5/1994 | Newton et al. |
| 5,372,596 A | 12/1994 | Klicek et al. |
| 5,432,459 A * | 7/1995 | Thompson et al. ............ 324/713 |
| 5,436,566 A | 7/1995 | Thompson et al. |
| 5,688,269 A | 11/1997 | Newton et al. |
| 5,769,841 A | 6/1998 | Odell et al. |
| 5,895,386 A | 4/1999 | Odell et al. |
| 5,936,536 A | 8/1999 | Morris |
| 6,245,063 B1 | 6/2001 | Uphoff |
| 6,494,877 B2 * | 12/2002 | Odell et al. ........................ 606/1 |
| 2001/0031992 A1 | 10/2001 | Fishler et al. |
| 2002/0161306 A1 | 10/2002 | Govari |
| 2003/0233088 A1 * | 12/2003 | Ohyama et al. .................. 606/46 |
| 2004/0015163 A1 * | 1/2004 | Buysse et al. .................... 606/34 |
| 2007/0173811 A1 | 7/2007 | Couture et al. |
| 2011/0221463 A1 | 9/2011 | Livneh |

OTHER PUBLICATIONS

The Electroscope Electroshield System; Electroscope, Inc. Boulder, CO; Sep. 7, 2000.

\* cited by examiner

LAPAROSCOPIC ELECTROSURGICAL ELECTRICAL LEAKAGE DETECTION

This application is a continuation-in-part application of U.S. application Ser. No. 13/355,729 filed Jan. 23, 2012, now U.S. Pat. No. 8,226,640, which is a continuation application of U.S. application Ser. No. 12/056,436 filed Mar. 27, 2008, now U.S. Pat. No. 8,100,897, the contents of which are hereby incorporated by reference in their entireties.

BACKGROUND

1. Field

The present disclosure relates generally to electrosurgery and electrosurgical systems and apparatuses, and more particularly, to an electrical leakage detection method and system for use with laparoscopic electrosurgical instruments.

2. Description of the Related Art

The term "laparoscope" comes from two Greek words. The first is lapara, which means "the soft parts of the body between the rib margins and hips", or more simply, the "flank or loinn". The other Greek root is skopein, which means "to see or view or examine". Skopein has become scope in English. Therefore, a laparoscope is an instrument through which structure within the abdomen and pelvis can be seen. A small surgical incision is made in the abdominal wall to permit the laparoscope to enter the abdomen or pelvis. A diversity of tubes can be pushed through the same incision or other small incisions permitting the introduction of probes and other instruments. In this way, a number of surgical procedures can be performed without the need for a large surgical incision. Among the instruments used during a laparoscopic procedure are electrosurgical instruments.

Laparoscopic surgery, a "minimally invasive" procedure, is commonly (but not exclusively) used to treat diseases of the gastrointestinal tract. Unlike traditional surgery on the colon or other parts of the intestines where a long incision down the center of the abdomen is required, laparoscopic surgery requires only a small "keyhole" incision in the abdomen. As a result, the person undergoing the procedure may experience less pain and scarring after surgery, and a more rapid recovery.

Electrosurgery is a term used to describe the passage of high-frequency (i.e., radio frequency) electrical current through tissue to create a desired clinical tissue effect. Through this technique, the target tissue, acting as a resistor in an electrical circuit, is heated by its conduction of the electrical current. Electrocautery, as distinguished from electrosurgery, uses an electrical current to heat a surgical instrument, which in turn conveys that heat to the target tissue. Electrosurgical electrode tips remain cool while targeted tissues heat up, primarily because the electrodes have much lower impedance than the adjacent targeted tissues. Electrosurgical tissue effects include cutting, coagulation, desiccation and fulguration. In addition, modern electrosurgical generators can create blended modes of operation under which a surgeon can for example, cut and coagulate simultaneously.

In electrosurgery, there are two types of electrodes: monopolar and bipolar. Mono-polar electrodes pass RF electrical current from an electrosurgical generator through an active electrode into targeted tissue, through the patient, the dispersive electrode (e.g., a return electrode or pad), and back into the electrosurgical generator. If the return electrode is properly placed relative to the patient and surgical site, the electrosurgical tissue effects occur only at the active electrode and not the dispersive electrode. On the other hand, bipolar electrodes are arranged in pairs (or poles, "+/−" and "−/+") and form part of the surgical instrument (e.g., electrosurgical forceps) without the need for a separate return electrode (grounding) plate attached to the patient. The intended flow of current is between the pair of bipolar electrodes (from "+/−" to "−/+"), which are usually close together and use relatively low voltage.

There are a number of well-known complications that may arise during laparoscopic electrosurgery. There are two major types of such complications pertinent to this discussion. The first derive from injuries caused by operator (i.e., surgeon) error such as direct coupling, perforation and laceration of targeted and non-targeted tissues. These injuries are outside the scope of this discussion. The second group of complications occurs when targeted tissues get burned from stray electricity emitting from or caused by other than operator error. There are two primary types of stray electricity applicable here.

The first type, insulation failure, involves faults in the insulation of the electrosurgical instrument—even a microscopic defect—that permit leakage of electrical current. The coating over metallic electrosurgical instruments intended to insulate then can be weakened by (i) repeated insertions into and removals from the patient, (ii) use of high voltage, (iii) material defects, and (iv) multiple sterilizations. A small hole in the insulation can represent a higher risk of injury from stray current than a larger hole because of its concentrating effect on the current density for such a leakage.

The second type of stray electricity results from capacitive coupling. Capacitive coupling occurs through instantaneous current induction between instruments, or between an instrument and adjacent tissues. This phenomenon can occur even though the insulation is completely intact. Capacitive coupling requires a capacitor, which is created when two conductors are separated by an insulator. The risk of this type of stray electricity can increase when surgeons use disposable and reusable instruments together during the same laparoscopic electrosurgical procedure.

The clinical complications from stray current caused by insulation failure and capacity coupling are particularly challenging because their initial presentation often mimics normal post-surgical symptoms of laparoscopy: namely, non-specific abdominal pain and slight to moderate fever. These clinical complications include perforation, blood vessel damage, organ damage, and peritonitis. All of these, particularly fecal peritonitis, can lead to severe or fatal infection. Since injuries resulting from stray current are most often undiscovered until days after surgery, and are often masked by unrelated conditions, prevention of these injuries cannot be overstressed.

SUMMARY

An electrical leakage detection method and system for use with laparoscopic electrosurgical instruments are provided. In particular, this disclosure concerns of the unique aspects of laparoscopic electrosurgical electrical leakage detection and the prevention of unintended injuries to non-targeted tissues.

In one aspect of the present disclosure, an electrosurgical apparatus for use with an electrosurgical generator is provided including a handpiece having a passage extending therethough, the hand piece having a proximal end and a distal end; an active electrode having a tip and being adapted for coupling to said electrosurgical generator and extending through the passage for effecting at the tip thereof an electrosurgical procedure; a first sensor disposed at the distal end of the handpiece and for outputting a first signal indicative of current measured at the distal end; a second sensor disposed at the proximal end of the handpiece and for outputting a second signal indicative of current measured at the proximal end; and a differential device coupled to the first and second sensors for receiving the first and second signals and determining a difference value of the first and second signal, the difference value being indicative of leakage current.

In another aspect of the present disclosure, an electrosurgical system for controlling leakage during electrosurgical procedure is provided. The electrosurgical system includes an electrosurgical unit for providing electrosurgical energy at an active output thereof and for controlling the flow of the energy through the active output, the electrosurgical unit having a return input; an active electrode coupled to the active output for transmitting electrosurgical energy to a patient in an electrosurgical procedure; a return electrode adapted to be coupled to the patient for receiving electrosurgical energy supplied to the patient during the electrosurgical procedure and coupled to the return input for returning it to the return input of the electrosurgical unit; a first sensor disposed at a distal end of the active electrode and for outputting a first signal indicative of current measured at the distal end; a second sensor disposed at a proximal end of the active electrode and for outputting a second signal indicative of current measured at the proximal end; and a comparison circuit coupled to the first and second sensors for receiving the first and second signals and determining a difference value of the first and second signal, the difference value being indicative of leakage current.

In a further aspect of the present disclosure, an endoscopic forceps for effecting tissue includes an elongated shaft having opposing jaw members at a distal end thereof, the jaw members being movable relative to one another from a first position wherein the jaw members are disposed in spaced relation relative to one another to a second position wherein the jaw members cooperate to grasp tissue therebetween; a handle assembly coupled to a proximal end of the shaft for actuating the jaw members between the first and second positions; each jaw member including an electrically conductive surface and adapted to electrically couple to a source of electrical energy such that the jaw members are capable of conducting energy to tissue held therebetween to effect an electrosurgical procedure; a first sensor disposed at the distal end of the shaft and for outputting a first signal indicative of current measured at the distal end; a second sensor disposed at the proximal end of the shaft and for outputting a second signal indicative of current measured at the proximal end; and a differential device coupled to the first and second sensors for receiving the first and second signals and determining a difference value of the first and second signal, the difference value being indicative of leakage current.

In yet another aspect of the present disclosure, an apparatus for use with an endoscopic applicator is provided, the endoscopic applicator including a shaft having a proximal end and a distal end and an active electrode having a tip and being adapted for coupling to an electrosurgical generator and extending through the shaft for effecting at the tip thereof an electrosurgical procedure, the apparatus including: a support member configured to be coupled to the shaft; a first sensor disposed on the distal end of the support member and for outputting a first signal indicative of current measured at the distal end of the active electrode; and a second sensor disposed on the proximal end of the support member and for outputting a second signal indicative of current measured at the proximal end of the active electrode, wherein a difference value of the first and second signal is indicative of leakage of current within the shaft.

In one aspect, the first and second sensors are magnetic sensors.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
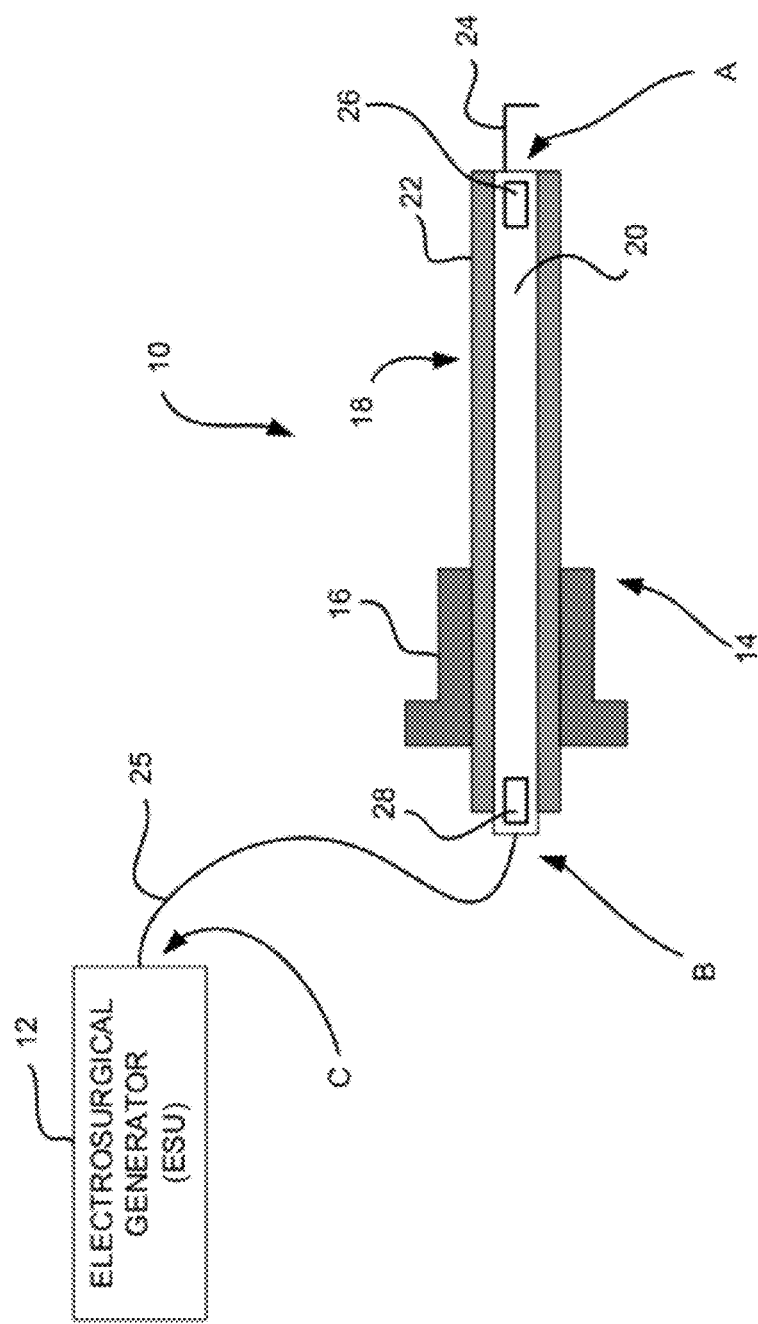
FIG. 1 is an illustration of a laparoscopic electrosurgical system in accordance with an embodiment of the present disclosure.

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

An electrical leakage detection method and system for use with laparoscopic electrosurgical instruments are provided. The techniques of the present disclosure provide for: (a) detecting the occurrence of an electrical leakage event (e.g., stray electrical current) during laparoscopic electrosurgery, (b) instantly shutting down the electrosurgical generator to prevent stray electrical current injury to the patient, and (c) warning the operator of an electrical leakage incident. Some in the field have used multiple layers of insulation in an attempt to avoid the electrical leakage problem caused by insulation failure; however, this approach, even if fully effective, does not address the capacitive coupling problem. Others have employed methods to detect a loss of contact between the patient and the grounding pad used in mono-polar electrosurgery. Still others have used methods that relay on measurements within the electrosurgical generator, and not in or near the electrosurgical instruments themselves. However, such measures do not adequately address the specific problem of electrical leakage from laparoscopic electrosurgical instruments.

Rather than employing such approaches, the system and method of the present disclosure seeks to measure the electrical current at two key points along the path of electrosurgical current created by the electrosurgical generator, the power cord connecting the laparoscopic instrument body, the laparoscopic instrument body, and the electrode tip.

Referring to FIG. 1, an electrosurgical system 10 is shown including an electrosurgical generator (ESU) 12 and a larascopic instrument 14. The electrosurgical generator 12 is configured for supplying electrosurgical energy via a laparoscopic instrument 14 to an operative site of a patient, e.g., tissue. The electrosurgical laparoscopic apparatus 14 includes a trocar sheath or cannula 16 which is conventionally used to provide a conduit through a patient's skin into the peritoneal cavity. Removably insertable through the trocar sheath is an active electrode probe or handpiece 18 which includes an active electrode 20 disposed within a passage of the handpiece and an insulative coating 22 thereon. The distal end of the electrode 20 includes a tip 24 for affecting a surgical procedure at the operative site. The tip 24 of the probe may be of different conventional shapes such as needle-shape, hook-shape, spatula-shape, graspers, scissors, etc. and serve various conventional functions such as suction, coagulation, irrigation, pressurized gas, cutting, etc. Furthermore, the instrument 14 is coupled to the generator 12 via a power cord cable 25.

In FIG. 1, the first test point is at or very near the electrode tip 24 (Location "A"), e.g., a distal end of the instrument 14. The second test point is at the connection power cord's entry point into the laparoscopic instrument or just before it (Location "B"), e.g., a proximal end of the instrument 14. Then, by comparing the measured current at these two test points "A" and "B", the electrosurgical generator 12 can determine if there is a drop in output current, impliedly indicating electrical leakage. Conventional electrosurgical generator systems are capable of measuring output voltage (and other electrosurgical parameters such as tissue impedance) at the rate of 5 KHz. Given that very high rate, an automated decision to shut down the generator could occur very rapidly—virtually instantaneously—and thereby protect the patient from stray electrical current.

It is to be appreciated that the measurements taken at points "A" and "B" can be measured by a sensor 26 disposed adjacent the distal end of instrument 14 and sensor 28 disposed adjacent the proximal end of the instrument 14. As will be described below, the sensors 26, 28 may include a current sensor, resistor, or the like. The sensors 26, 28 will transmit the measured values to the electrosurgical generator 12 via hardwire or wireless means. In one embodiment, conductors carrying the measured values at Locations A and B are disposed in cable 25. In a further embodiment, the sensors 26, 28 will transmit the measured values via an RF signal to a receiver disposed in the electrosurgical generator 12.

In a further embodiment, the instrument 14 will include a differential device, e.g., a comparator, differential amplifier, etc., that determines the difference value and transmits a single difference value to the electrosurgical generator 12.

It is further to be appreciated that the second test point may be measured at the electrosurgical generator 12 (Location "C"). In this embodiment, the sensor is disposed in the electrosurgical generator 12 and measured the current leaving the generator 12. The leakage current is then determined by calculating the difference between the current measured at Location A and Location C. In this embodiment, only sensor 26 is disposed in the instrument 14 resulting in a lower cost instrument.

Figure 2:
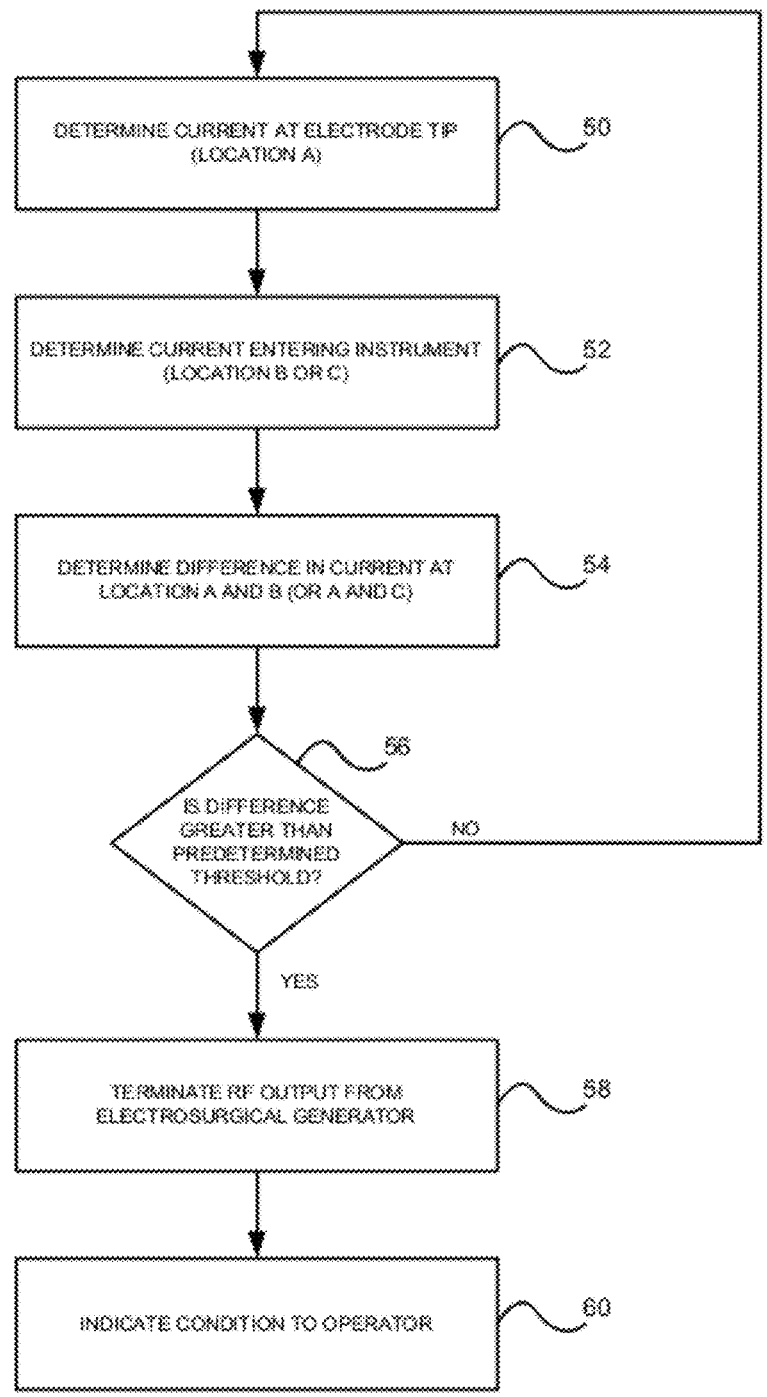
FIG. 2 is a flow diagram of a method for detecting leakage current in an electrosurgical system in accordance with an embodiment of the present disclosure.

Referring to FIG. 2, a method for detecting leakage current in an electrosurgical system is illustrated. Initially, at step 50, current is determined at the electrode tip 24, i.e., Location A. Next, the current entering the instrument, i.e., Location B, is determined in step 52. It is to be appreciated that in certain embodiments the current entering the instrument will be measured as current leaving the electrosurgical generator 12, i.e., Location C. Next, in step 54, a difference in the current measured at Locations A and B is determined.

In step 56, it is determined if the difference is greater than a predetermined threshold. If the difference is less than the predetermined threshold, no leakage current has been detected, or an acceptable amount of leakage current has been detected, and the method will revert to step 50 to continue to monitor the current at Locations A and B. If the difference is greater than the predetermined threshold, leakage current has been detected. When leakage current has been detected, the RF output from the electrosurgical generator 12 will be terminated in step 58. Furthermore, in step 60, the electrical leakage condition will be indicated to the operator, e.g., a surgeon, via the electrosurgical generator 12 or laparoscopic instrument 14. It is to be appreciated that steps 58 and 60 may be performed simultaneously and/or step 60 may be performed before step 58.

Alternative embodiments for the system of the present disclosure will be described below. The various embodiments focus on the technique of measuring voltage, calculating current, and comparing those values between Locations "A" and "B", as described above.

Figure 3:
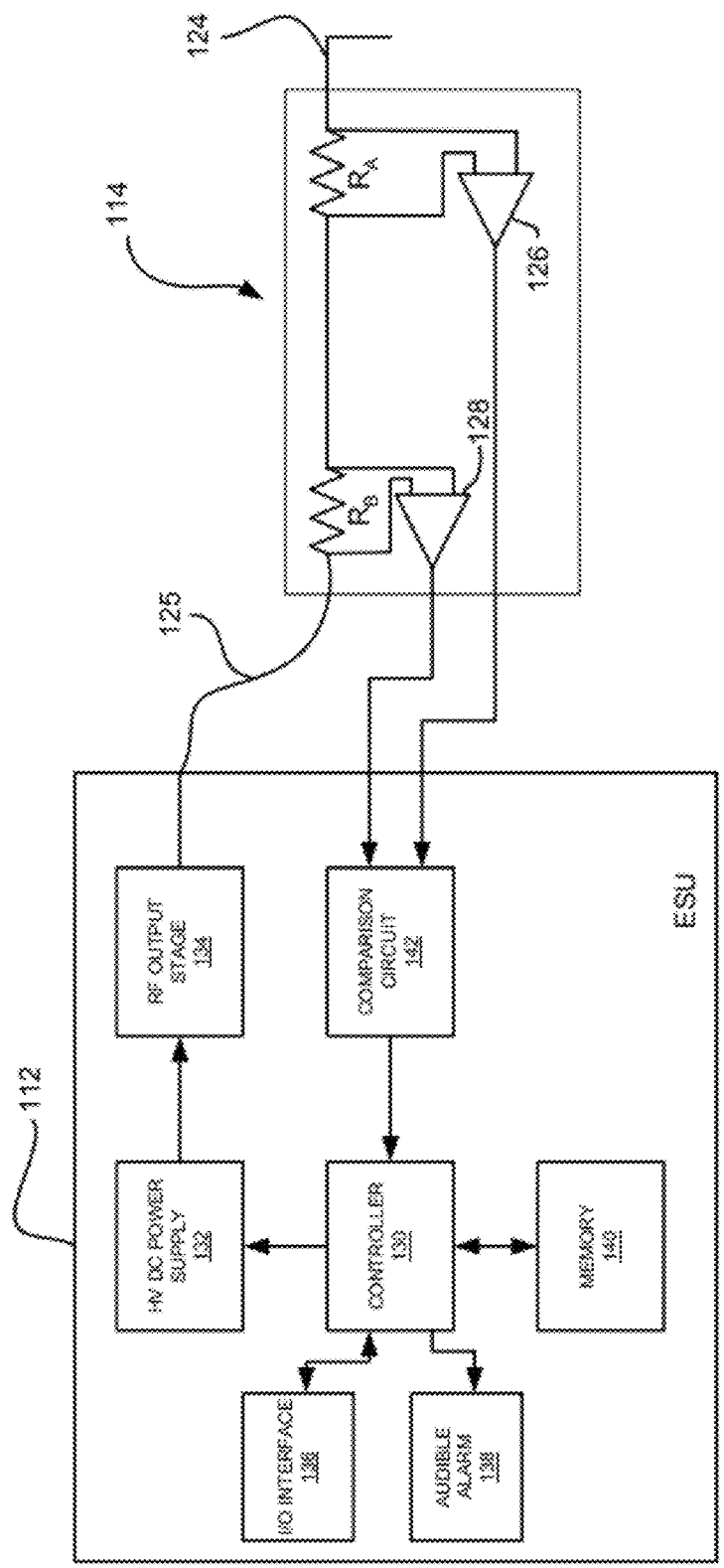
FIG. 3 is a block diagram of an electrosurgical generator and laparoscopic instrument in accordance with an embodiment of the present disclosure.

Referring to FIG. 3, one embodiment of the system contemplates placement of a series resistor ($R_A$) at Location "A" in instrument 114. Using Ohm's Law (i.e., V=IR, where V is voltage, I is current, and R is resistance), the current $I_A$ for a measured voltage $V_A$ can be calculated. Thus, $I_A=V_A/R_A$. The challenge with this design is the need to transfer the calculated value of current at Location A ($I_A$) back to the generator. One solution is to place means of converting $I_A$ from an analog to a digital value, which can then be transmitted back to the generator, free from electrical or magnetic interference. In one embodiment, an analog to digital converter ADC 126 may be coupled to resistor $R_A$ for transmitting the measured voltage across resistor $R_A$ to electrosurgical generator 112. The digital signal will be sent to a controller 130, e.g., a microprocessor, which can determine a current value from the measured voltage. Thus, by converting the value to the digital domain, rapid and accurate monitoring of current can be maintained. The same technique could be employed at Location B with a second series resistor $R_B$ and second ADC 128. As described above, the measured values may be transmitted to the generator 112 via conductors or other known transmission means in cable 125, or alternatively, may be bundled in a second cable separate from the power cable 125. If a leakage condition is detected, the controller 130 will control the HV DC power supply 132 to terminate the electrosurgical energy being output from the RF output stage 134. Furthermore, as described above, the electrosurgical generator 112 will indicate the condition to an operator via an I/O interface 136 such as a touch screen or an audible alarm 138.

In a further embodiment, the electrosurgical generator 112 includes a comparison circuit 142 that receives the signals from the sensors disposed in the instrument 114. The comparison circuit 142 determines the difference between the received signals and transmits a single difference value to the controller 130. The controller 130 then determines if the difference value is greater than a predetermined threshold. If so, the controller 130 will terminate the output of electrosurgical energy by controlling the HV DC power supply 132.

It is expected that each combination of generator 112 and connecting power cord 125 to the instruments 114 will exhibit some inherent resistance. Accordingly, there will be a correction factor for that combination stored in a memory 140 of the generator 112. Differences between calculated current values at Locations A and B, adjusted by the correction factor, indicate a loss of current suggesting electrical leakage. Based on preset thresholds, the generator 112 can detect a threshold difference, set an alarm and shut down the generator. In this way, the patient can be protected from unintended injury (e.g., burns) from stray current.

Figure 4:
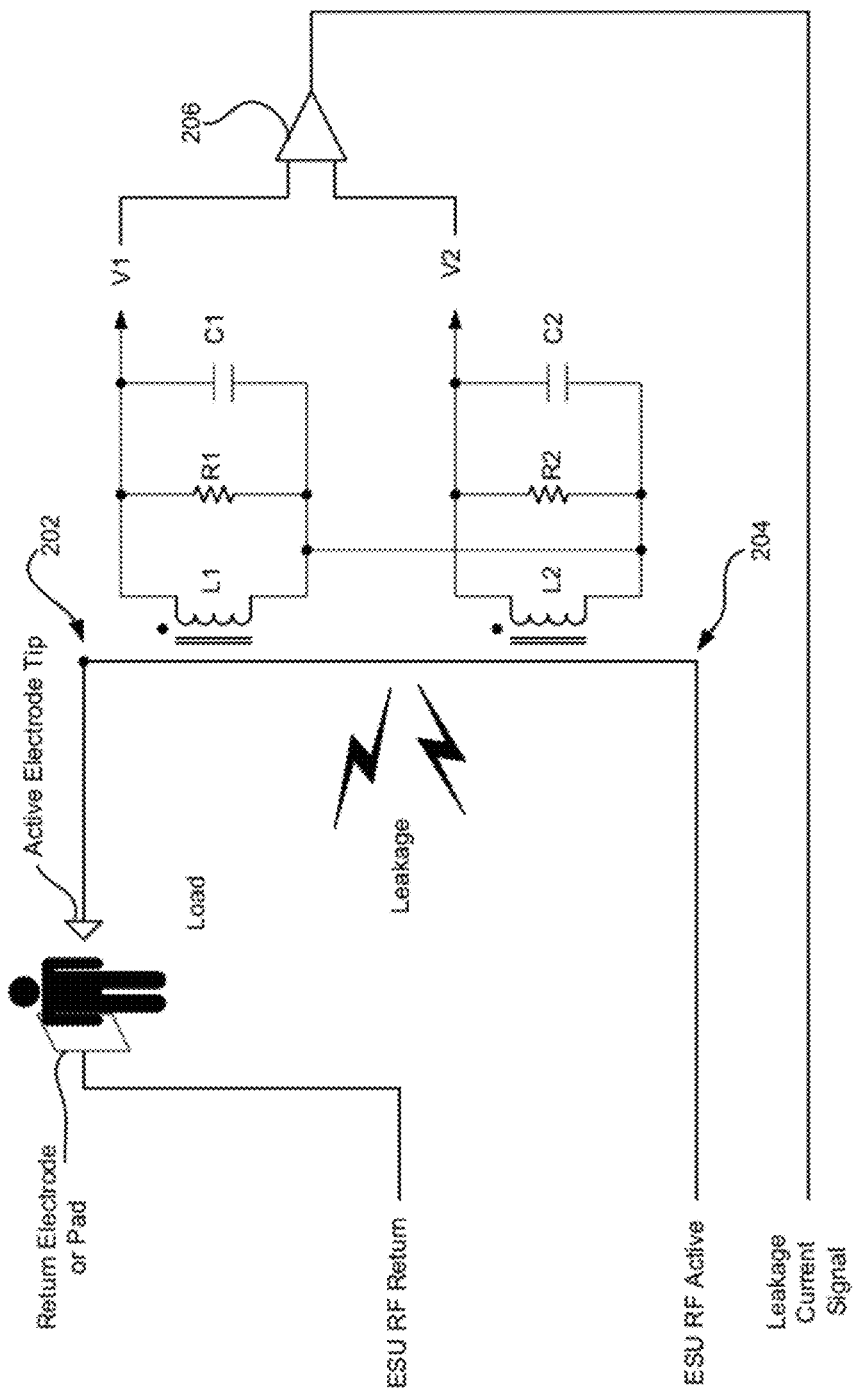
FIG. 4 is a schematic diagram of a laparoscopic instrument for detecting leakage current in accordance with an embodiment of the present disclosure.

In another embodiment, a dual current sensing transformer arrangement, both with the same turns ratio, is used in combination with means for converting analog measurements to digital values, as shown in FIG. 4. In this embodiment, a first distal coil L1 can be constructed from the conductor material itself within the instrument body at a distal end 202. A second proximal coil L2 is then formed and placed at a proximal end 204 of the instrument. The induced current in the coil L1 is converted to voltage V1 via resistor R1 and capacitor C1 which are coupled in parallel. Similarly, induced current in coil L2 is converted to voltage V2 via resistor R2 and capacitor C2. The difference between voltage V1 (indicative of the current induced in the distal coil L1) and voltage V2 (indicative of the current induced in the proximal coil L2) can then be measured, digitized and transmitted back to the generator via analog-to-digital converter ADC 206. By using two identical transformers and passing high current through them, the system of the present disclosure can achieve improved noise immunity and measurement accuracy.

Another embodiment according to the present disclosure includes a monopolar forceps for affecting tissue having an elongated shaft with opposing jaw members at a distal end thereof. The jaw members are movable relative to one another from a first position wherein the jaw members are disposed in spaced relation relative to one another to a second position wherein the jaw members cooperate to grasp tissue therebetween. By utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to the same electric potential such that when the jaw members grasp tissue, electrical energy can be selectively transferred to the tissue.

Figure 5:
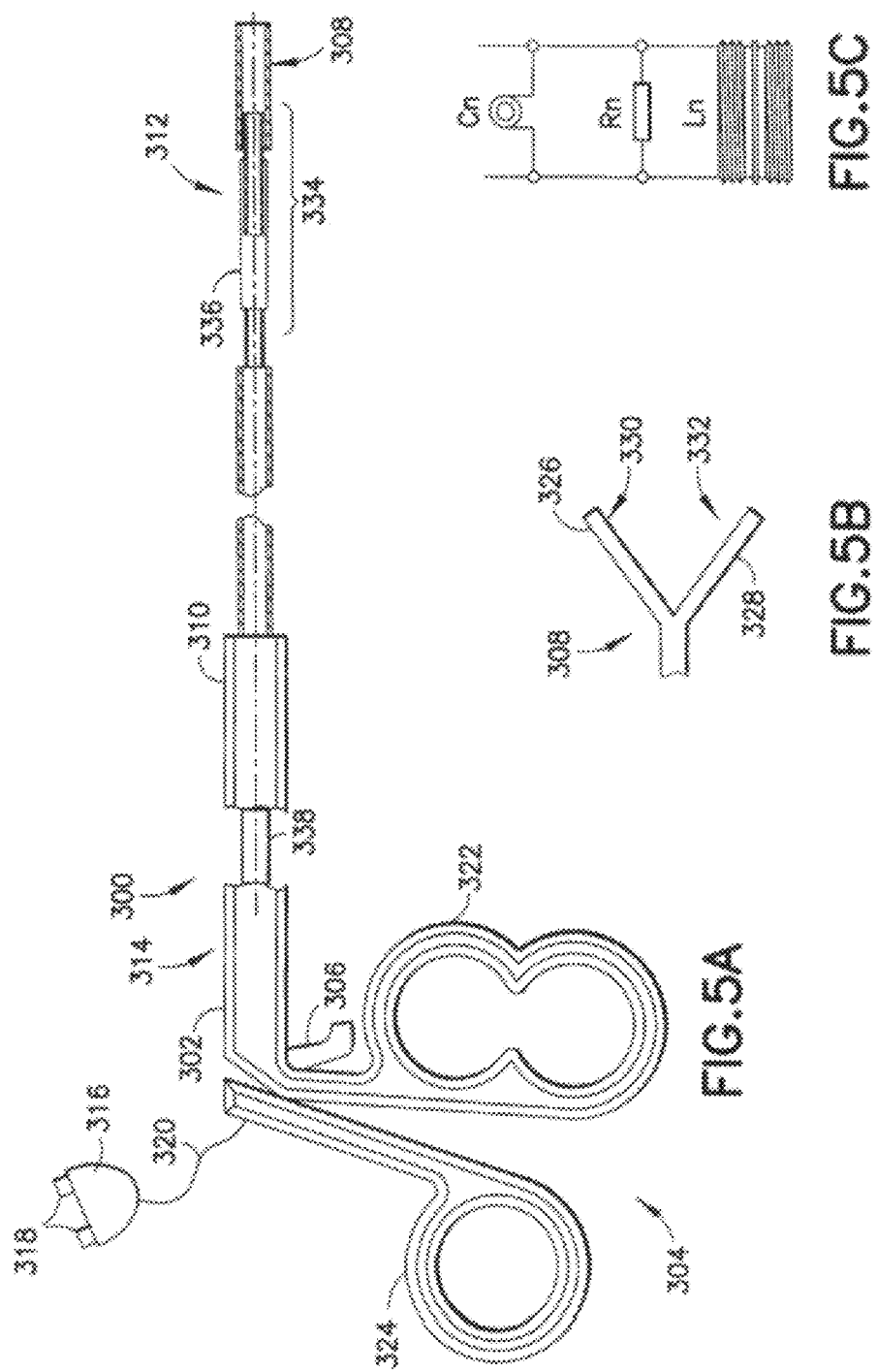
FIG. 5A is a partial cross sectional view of an electrosurgical bipolar forceps in accordance with an embodiment of the present disclosure.
FIG. 5B illustrates an end effector assembly of the bipolar forceps shown in FIG. 5A in an open position.
FIG. 5C is a schematic diagram of a current sensor in accordance with the present disclosure.

Referring to FIG. 5, one embodiment of a monopolar forceps 300 is shown for use with various surgical procedures and generally includes a housing 302, a handle assembly 304, a trigger assembly 306 and an end effector assembly 308 which mutually cooperate to grasp, seal and divide tubular vessels and vascular tissue. More particularly, forceps 300 includes a shaft 310 which has a distal end 312 dimensioned to mechanically engage the end effector assembly 308 and a proximal end 314 which mechanically engages the housing 302.

Forceps 300 also includes an electrical interface or plug 316 which couples the forceps 300 to a source of electrosurgical energy, e.g., a generator. Plug 316 includes a pair of prong members 318 which are dimensioned to mechanically and electrically couple the forceps 300 to the source of electrosurgical energy. An electrical cable 320 extends from the plug 316 to the forceps 300. Cable 320 is coupled to conductor 334 which extends along the shaft and is further coupled to the conducting surfaces of the end effector assembly 308.

Handle assembly 304 includes a fixed handle 322 and a movable handle 324. Fixed handle 322 is integrally associated with housing 302 and handle 324 is movable relative to fixed handle 322 to effect operation of the forceps 300.

As mentioned above, end effector assembly 308 is attached to the distal end 312 of shaft 310 and includes a pair of opposing jaw members 326 and 328. Movable handle 324 of handle assembly 304 is ultimately coupled to an actuation assembly (not shown) which, together, mechanically cooperate to impart movement of the jaw members 326 and 328 from an open position wherein the jaw members 326 and 328 are disposed in spaced relation relative to one another, to a clamping or closed position wherein the jaw members 326 and 328 cooperate to grasp tissue therebetween. Once the tissue is grasped, electrosurgical energy will be applied in response to trigger 306 or a footswitch coupled to the generator.

As mentioned above, the cable lead extend through the shaft 310 conducting electrosurgical energy from the generator to the jaw members 326, 328 of the end effector assembly 308. As illustrated in FIG. 5B, each jaw member 326, 328 includes an internal conducting surface 330, 332 respectively for contacting tissue therebetween. In one embodiment, the cable 334 is coupled to and supplies electrosurgical energy to the two conducting surfaces 330, 332. In this manner, the conducting surfaces 330, 332 are the active electrode and a return electrode, e.g., a return pad, is coupled to the patient for returning electrosurgical energy to the generator.

Referring back to FIG. 5A, a first current sensor 336, i.e., distal current sensing transformer, is disposed around the cable 334, i.e., the active electrode conductor, adjacent the distal end 312 of the shaft 310. A second current sensor 338, i.e., proximal current sensing transformer, is disposed around the cable 334 adjacent the proximal end 314 of the shaft 310. Referring to FIG. 5C, the first and second current sensors 336, 338 include a capacitor Cn, a resistor Rn and a toroidal or hollow cylindrical core inductor Ln. It is to be appreciated the capacitor Cn, resistor Rn and inductor Ln will be disposed in the housing 302. The first and second current sensors 336, 338 will operate in cooperation to determine the difference in current, i.e., leakage current, between the distal end of the instrument and proximal end in accordance with the various embodiments described above.

It is envisioned that the forceps 300 may be designed such that it is fully or partially disposable depending upon a particular purpose or to achieve a particular result. For example, end effector assembly 308 may be selectively and releasably engageable with the distal end 312 of the shaft 310 and/or the proximal end 314 of shaft 310 may be selectively and releasably engageable with the housing 302 and the handle assembly 304. In either of these two instances, the forceps 300 would be considered "partially disposable" or "reposable", i.e., a new or different end effector assembly 308 (or end effector assembly 308 and shaft 310) selectively replaces the old end effector assembly 308 as needed.

In a further embodiment, the instrument shown in FIG. 5A will be configured as bipolar forceps. Although not shown, in the bipolar embodiment, cable 320 is internally divided into two cable leads, e.g., first and second cable leads, which transmit electrosurgical energy through their respective feed paths through the forceps 300 to the end effector assembly 308. Here, the electrode of each jaw member is charged to a different electric potential such that when the jaw members grasp tissue, electrical energy can be selectively transferred through the tissue.

In the bipolar embodiment, the first and second cable leads extend through the shaft 310 conducting electrosurgical energy from the generator to the jaw members 326, 328 of the end effector assembly 308. Similar to the embodiment described above in relation to FIG. 5B, each jaw member 326, 328 includes an internal conducting surface 330, 332 respectively for contacting tissue therebetween. The first cable 334 is coupled to and supplies electrosurgical energy to conducting surface 330 while the second cable (not shown) is coupled to conducting surface 332 and returns the electrosurgical energy to the generator. In this manner, the conducting surface 330 is the active electrode and the conducting surface 332 is the return electrode, i.e., no additional return pad is necessary.

In the bipolar embodiment, a first current sensor 336 is disposed around the cable 334, i.e., the active electrode conductor, adjacent the distal end 312 of the shaft 310 and a second current sensor 338 is disposed around the cable 334 adjacent the proximal end 314 of the shaft 310, similar to the embodiment described above in relation to the monopolar embodiment. The first and second current sensors 336, 338 are configured as shown in FIGS. 5A and C. The first and second current sensors 336, 338 will operate in cooperation to determine the difference in current, i.e., leakage current, between the distal end of the instrument and proximal end in accordance with the various embodiments described above.

While the previous embodiments are useful in detecting leakage currents in an endoscopic applicator, the above-described embodiments are built-in to the device during assembly or manufacture. A retrofit endoscopic leakage detector would allow the enhanced safety features of the present disclosure to be applied to pre-existing endoscopic applicators. There are two design challenges to the retrofit approach. One is the need to monitor the current in a non-contact fashion outside the insulating tube of an endoscopic applicator. Another is the need to have a very low profile as an add-on device since there is very little clearance available (about 0.5 mm) between the outer diameter (OD) of the insulating tube, and the inner diameter (ID) of a cannula or trocar.

In one embodiment, an external slip-on tube containing sensitive magnetic sensors at the proximal and distal sites is provided. Since the current flowing through a wire inside the insulating tube will produce a magnetic field, the sensing of this magnetic field can be used as a proxy for the current without having to break the circuit and insert a sensor. These currents are time varying alternating currents over a frequency range of a few hundred kHz up to a few MHz and will contain higher harmonics in pulse applications. Current RMS values can be up to 130 mA, while typically 40-45 mA. A new form of cold plasma jet endoscopic applicators can have currents up to 14 mA, but can be as low as a few mA.

The magnetic sensor can take various forms, such as a simple pick-up coil, or preferably, given the small size constraints, a magneto-resistance sensor. The magneto-resistance sensor changes its resistance in response to an applied magnetic field. It is constructed by depositing a thin layer of ferromagnetic material, such as iron or nickel, typically using vacuum deposition techniques. This is then followed by a very thin layer of non-ferromagnetic material, such as chromium or platinum, and then a final top thin layer of ferromagnetic material. Under applied magnetic field, electrons can easily pass through the very thin non-ferromagnetic layer. The stronger the magnetic field, the more easily these electrons can pass and so the overall resistance of the device will decrease with increasing magnetic fields. Magneto-resistance sensors have been constructed with several alternating layers of ferromagnetic and non-ferromagnetic materials, greatly enhancing the sensitivity of the sensor, and are referred to as Giant Magneto-Resistance, or GMR sensors. Due to their great sensitivity, only a very small sensing area is needed, which is ideal for the leakage detectors of the present disclosure.

Figure 6:
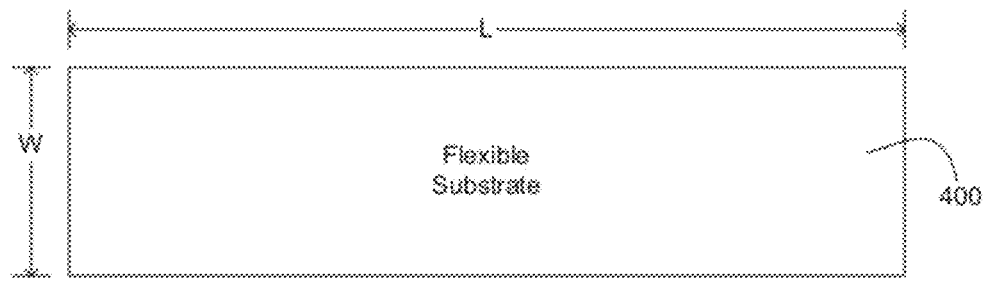
FIGS. 6-11 illustrates an exemplary method for fabricating a retrofit endoscopic leakage detector in accordance with the present disclosure.

Referring to FIGS. 6-12, a construction sequence is outlined below for an exemplary slip-on retrofit endoscopic applicator electrical leakage sensor tube in accordance with the present disclosure. Initially, a thin film substrate 400 (approximately 100 μm) which is flexible, low cost, and amenable to vacuum deposition procedures is provided. An exemplary substrate material is a polyimide such as Kapton™ which is strong, relatively low cost, has high dielectric strength, adding an additional safety factor, thermally stable and vacuum compatible. As illustrated in FIG. 6, the sheet 400 will have a length L equal the length of an endoscopic insulating tube to which it is to be applied, and a width W that is equal to the circumference of the insulating tube plus a small clearance to allow easy slip-on.

Figure 7:
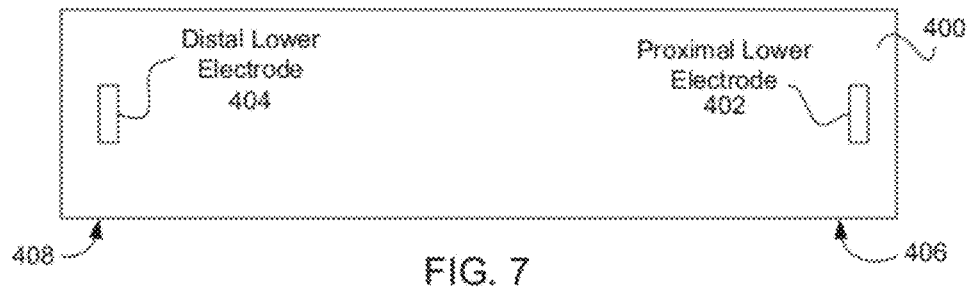
Figure 8:
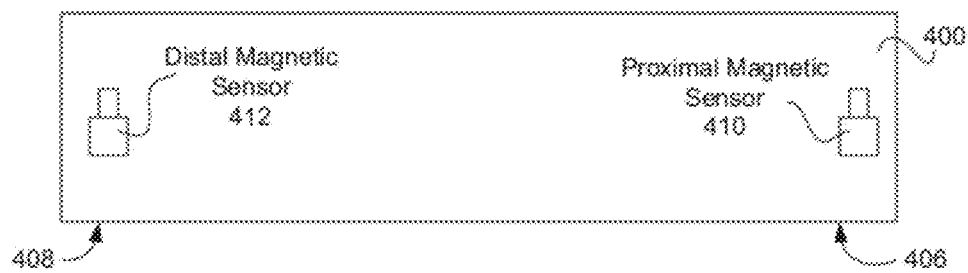
Figure 9:
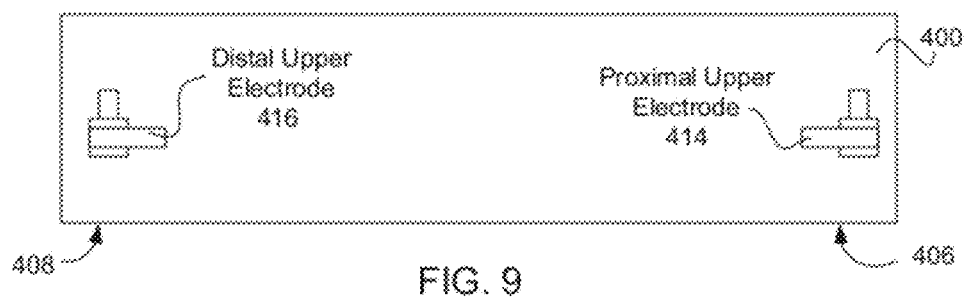

The first processing step will deposit two lower electrical contact pads or electrodes 402, 404 for the magnetic sensors at the proximal and distal sensing sites, 406 and 408 respectively, of the flexible substrate 400, as shown in FIG. 7. Note that these are shown for illustration purposes and not to scale. Next, as shown in FIG. 8, magnetic sensor material 410, 412 is deposited on a surface of the lower electrodes 402, 404, as described above. It is to be appreciated that the magnetic sensor material 410, 412 may be a multi-layer device. Then, an upper electrical contact 414, 416 is deposited on the magnetic sensors as illustrated in FIG. 9.

Figure 10:
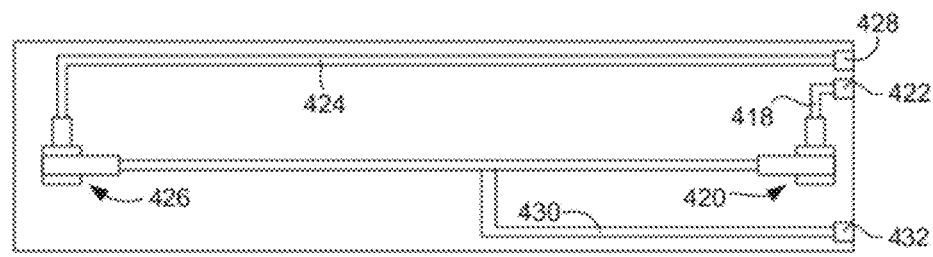

Electrical conductors which convey the magnetic sensor signals to an edge connector (on the proximal end 406) are deposited or screen printed, as shown in FIG. 10. Conductive trace 418 couples proximal magnetic sensor 420 to proximal sensor output 422. Conductive trace 424 couples distal magnetic sensor 426 to distal sensor output 428. Furthermore, conductive trace 430 couples both the proximal magnetic sensor 420 and distal magnetic sensor 426 to common output 432. A plurality of conductors couple the outputs 422, 428, 432 to an electrosurgical generator or other control electronics to control the output of electrosurgical energy to and from the endoscopic applicator according to the various techniques described above.

Figure 11:
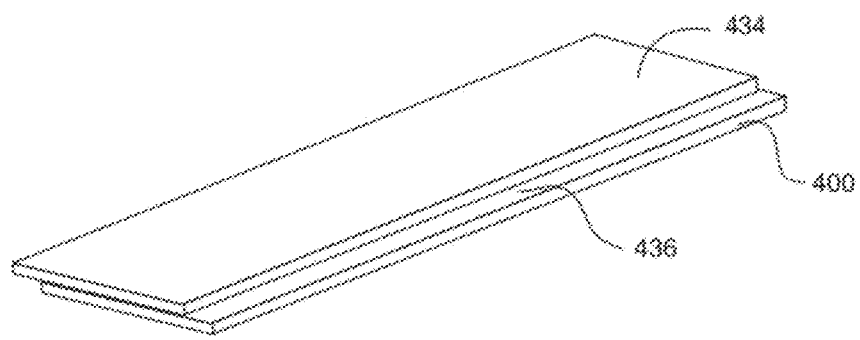
Figure 12:
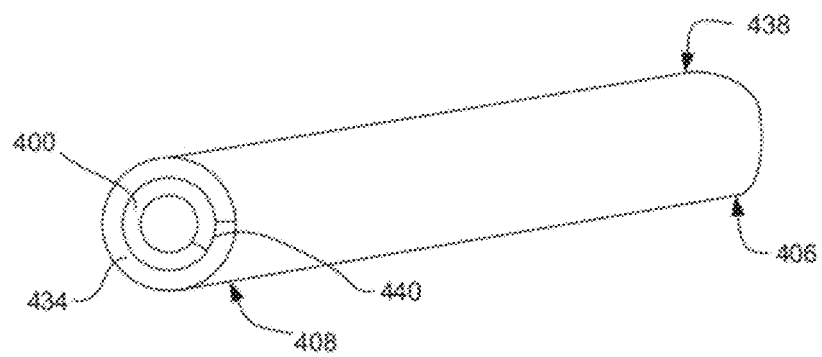
FIG. 12 illustrates a retrofit endoscopic leakage detector in accordance with the present disclosure.

A second thinner sheet 434 of polyimide (e.g., approximately 50 μm) is then attached over the substrate sheet 400 with the magnetic sensors as a protective layer. It is displaced to one side slightly to form a lap joint 436 as illustrated in FIG. 11. The two layer assembly is then rolled into a tube 438, adhesively joining the lap joint into an overlap region 440, as shown in FIG. 12. The combined thickness of the substrate 400 and protective sheet 434 adds approximately 300 μm to the OD of the endoscopic insulator tube, still allowing approximately 200 μm (0.2 mm) of clearance with the ID of the cannula or trocar.

In one embodiment, the edge connector mechanically engages a housing of a handpiece (e.g., handpiece shown in FIG. 5A), when the sensor tube is slid over the insulting tube, or shaft, of an endoscopic applicator. The housing may be adapted to receive the edge connector and control the output of the electrosurgical energy either in the handpiece or at the electrosurgical generator. In another embodiment, the edge connector may include a wireless transceiver for wirelessly communicating with a local electrosurgical generator.

Although not shown, a differential device that determines the difference in sensed parameters of the proximal magnetic sensor 420 and distal magnetic sensor 426 may be included on the substrate 400 as part of the sensor tube to reduce a number of wires or conductors between the sensor tube and the electrosurgical generator.

Figure 13:
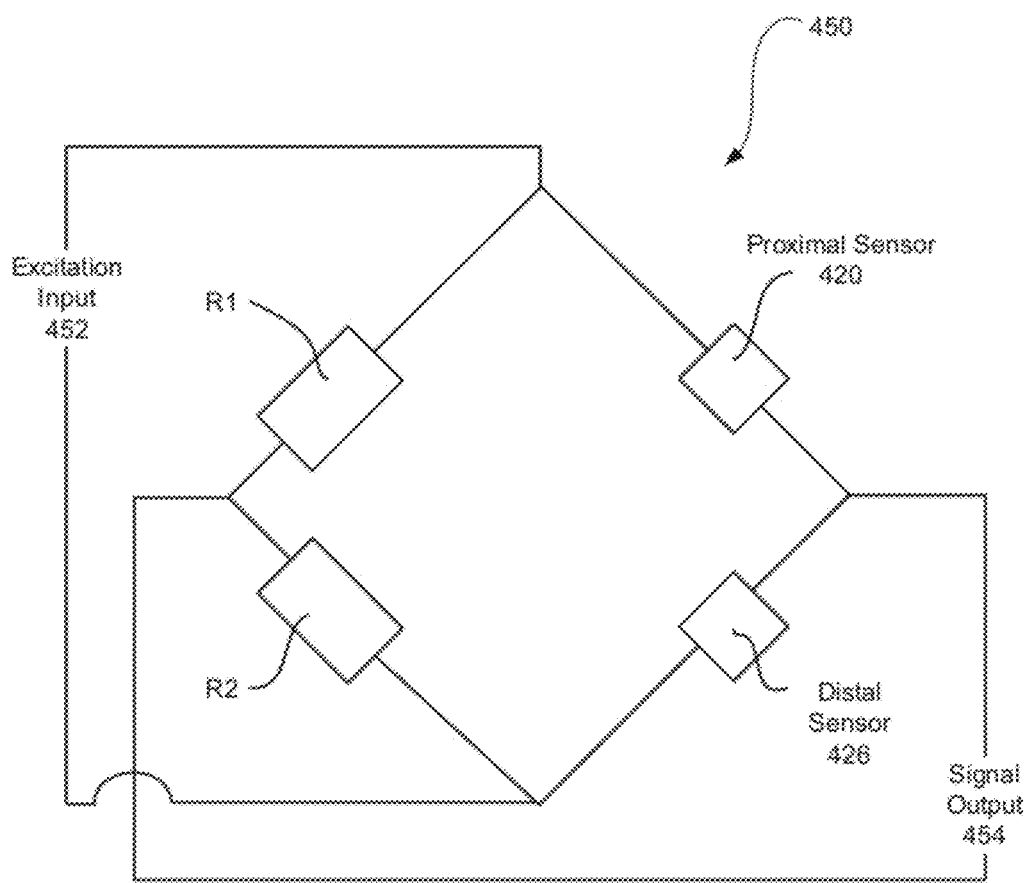
FIG. 13 illustrates a leakage detector employing magnetic sensors as part of a Wheatstone Bridge in accordance with an embodiment of the present disclosure.

Not shown are the attachment of support and conditioning circuitry for the magnetic sensors, and the use of a leakage detection signal. The support and conditioning circuitry may contain a Wheatstone Bridge using the magnetic sensors as two arms of the bridge, as a way of enhancing sensitivity of the overall system. Wheatstone Bridge 450 employing such a configuration is illustrated in FIG. 13. The proximal and distal sensors, e.g., sensors 420 and 426 respectively, form two arms of the bridge, while two equal value resistors R1 and R2 form the opposite arms. Typical values for resistors R1 and R2 would be in the range of the nominal operating resistance of the magnetic sensors. The excitation input 452 is typically a small DC voltage of a few volts. Under balanced bridge conditions, where the resistance of the two magnetic sensors is equal, there will be no output signal. In the event of a leakage current in the endoscopic applicator, the proximal and distal magnetic sensors will detect different magnetic fields, have different resistances, and unbalance the bridge. A voltage will then appear on the signal output 454 indicative of leakage current. The signal output may then be transmitted to an electrosurgical generator or other control circuitry to, for example, trigger an alarm condition or control the output of the endoscopic applicator. The resistors of the bridge can be mounted (or deposited) alongside the magnetic sensors.

Figure 14:
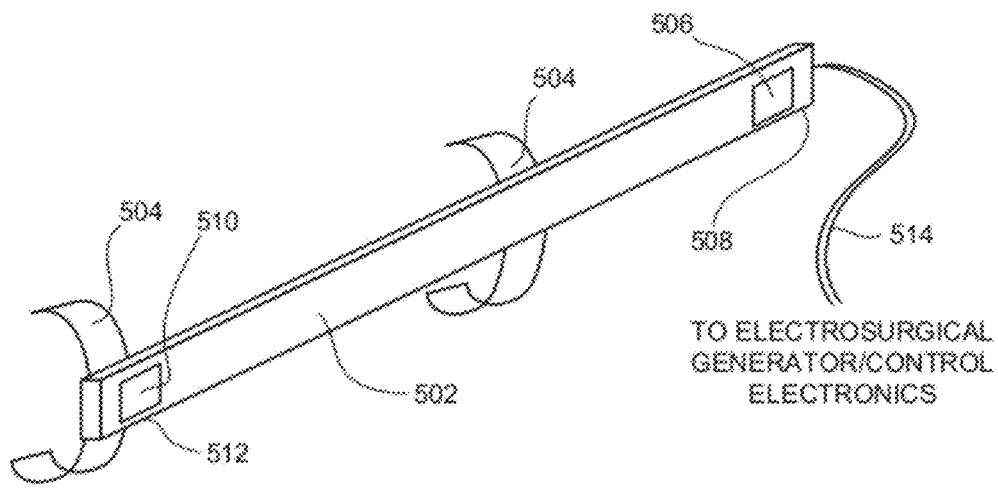
FIG. 14 illustrates a retrofit endoscopic leakage detector in accordance with another embodiment of the present disclosure.

It is to be appreciated that the retrofit leakage magnetic sensors need not be mounted on an entire slip-on tube, as illustrated in FIG. 12, but rather be part of an external support bar 502 which mounts to the exterior of the endoscopic applicator with the aid of one or more clips 504, as illustrated in FIG. 14. The support bar 502 includes a proximal sensor 506 disposed on a proximal end 508 of the support bar and a distal sensor 510 disposed on a distal end 512. Alternately, the support bar 502 can be attached to the endoscopic applicator adhesively or by other means, eliminating the need for clips 504. A cable 514 is provided to couple the sensors 506, 510 to an electrosurgical generator or other control electronics. Cable 514 may include individual conductors disposed within the support bar 502 or may include conductive traces along at least one surface of the support bar 502. It is to be appreciated that the support bar or member 502 is for illustrative purposes only and not shown to scale.

Figure 15:
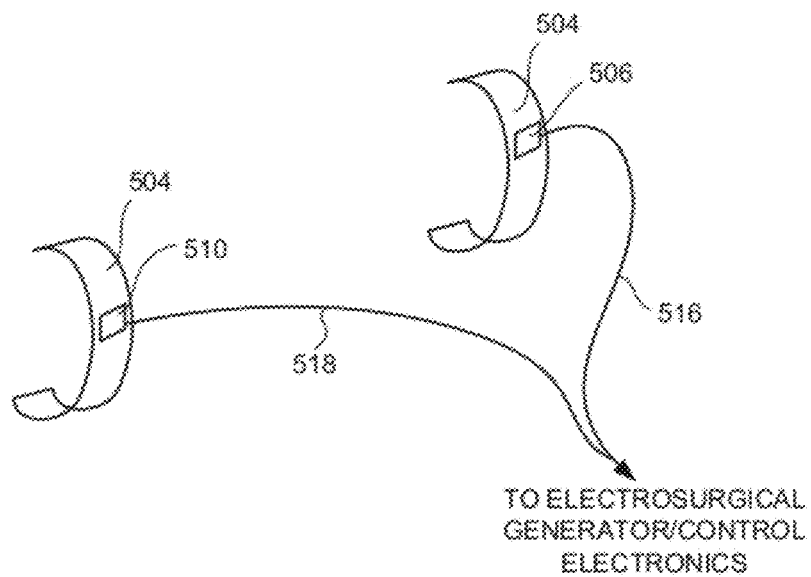
FIG. 15 illustrates a retrofit endoscopic leakage detector in accordance with a further embodiment of the present disclosure.

An even further simplification is possible with the magnetic sensors 506, 510 mounted directly to two clips 504 which can then be attached to the proximal and distal ends of the endoscopic applicator, respectively, as shown in FIG. 15. Similarly, the distal and proximal magnetic sensors themselves can be individually attached adhesively to the distal and proximal ends of the endoscopic applicator, without the need for clips. Conductors 516, 518 couple each of the magnetic sensors 506, 510 to an electrosurgical generator or other control electronics. Alternatively, each of the magnetic sensors 506, 510 communicates wirelessly to an electrosurgical generator or other control electronics.

Figure 16:
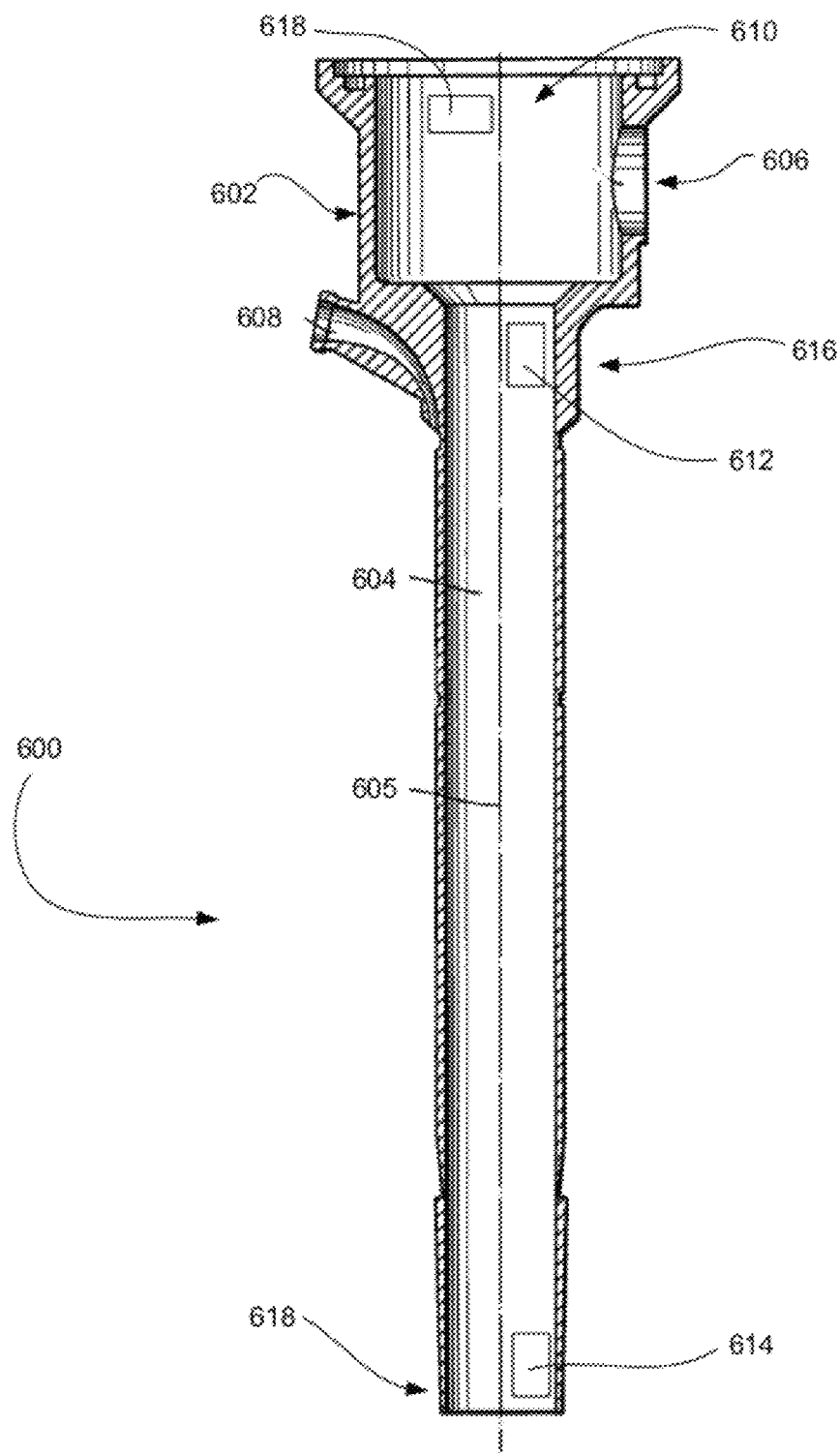
FIG. 16 illustrates a retrofit endoscopic leakage detector in accordance with another embodiment of the present disclosure.

In another embodiment, the teachings of the present disclosure may be incorporated into a cannula or trocar. In this embodiment, a magnetic sensor is disposed on each of the proximal and distal ends of a hollow sleeve of the cannula or trocar. As shown in FIG. 16, an exemplary cannula or trocar 600 includes a hub 602 connected to tubular member 604 aligned along a central axis 605. In certain embodiments, the hub 602 may include a port 606 for receiving valving and gas input components and a fluid input 608 for introduction of necessary or desired fluids to irrigate a surgical site. The hub 602 includes an opening 610 for receiving an elongated endoscopic applicator which is to be inserted into the tubular member 604. The tubular member 604 includes a proximal magnetic sensor 612 disposed at an upper or proximal end 616 and distal magnetic sensor 614 disposed at the lower or distal end 618. A signal indicative of leakage current may then be generated by any device inserted into the cannula or trocar 600 in accordance with the various techniques described in the present disclosure. For example, in one embodiment, the proximal and distal magnetic sensors 612, 614 may be wired to the hub 602 which includes conductors or wires for coupling the cannula or trocar 600 to an electrosurgical generator or other control electronics. In other embodiment, the proximal and distal magnetic sensors 612, 614 may be coupled, e.g., by conductive traces, to a wireless transceiver 618 disposed in the hub 602 for wirelessly communicating current or leakage signals to the electrosurgical generator or other control electronics. Optionally, a differential device that determines the difference in sensed parameters of the proximal magnetic sensor 612 and distal magnetic sensor 614 may be included in the hub 602 to reduce a number of wires or conductors between the cannula or trocar 600 and the electrosurgical generator/control electronics.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An apparatus for use with an endoscopic applicator, the endoscopic applicator including a shaft having a proximal end and a distal end and an active electrode having a tip and being adapted for coupling to an electrosurgical generator and extending through the shaft for effecting at the tip thereof an electrosurgical procedure, the apparatus comprising:
   a support member having a distal end and a proximal end configured to be coupled to an external surface of the shaft;
   a first sensor disposed on the distal end of the support member and for outputting a first signal indicative of current measured at a distal end of the active electrode; and
   a second sensor disposed on the proximal end of the support member and for outputting a second signal indicative of current measured at a proximal end of the active electrode,
   wherein a difference value of the first and second signal is indicative of leakage of current within the shaft.

2. The apparatus of claim 1, further comprising a differential device coupled to the first and second sensors for receiving the first and second signals and determining the difference value of the first and second signal.

3. The apparatus of claim 1, further comprising an analog to digital converter coupled to each of the first and second sensors.

4. The apparatus of claim 1, wherein each of the first and second signals is a digital signal.

5. The apparatus of claim 1, wherein the support member is a tube configured to be disposed around the shaft of the endoscopic applicator.

6. The apparatus of claim 1, wherein the support member is a bar coupled to the external surface of the shaft of the endoscopic applicator.

7. The apparatus of claim 1, wherein the support member includes a first clip for coupling the first sensor to the shaft of the endoscopic applicator and a second clip for coupling the second sensor to the shaft of the endoscopic applicator.

8. The apparatus of claim 1, further comprising at least one conductor coupled to the first and second sensors configured to transmit the first and second signals to the electrosurgical generator.

9. The apparatus of claim 1, further comprising a wireless transceiver coupled to the first and second sensors configured to transmit the first and second signals to the electrosurgical generator wirelessly.

10. An electrosurgical system for controlling leakage during electrosurgical procedure comprising:
   an electrosurgical unit for providing electrosurgical energy at an active output thereof and for controlling the flow of the energy through the active output, the electrosurgical unit having a return input;
   an active electrode coupled to the active output for transmitting electrosurgical energy to a patient in an electrosurgical procedure;
   a handpiece for supporting the active electrode, the handpiece including a housing and a shaft having a proximal end and a distal end, the proximal end of the shaft configured to be releasably engageable with the housing, wherein the active electrode is disposed within the shaft;
   a return electrode adapted to be coupled to the patient for receiving electrosurgical energy supplied to the patient during the electrosurgical procedure and coupled to the return input for returning it to the return input of the electrosurgical unit; a support member configured to be coupled to the shaft; and
   an electrical leakage detector comprising:
      a support member having a distal end and a proximal end configured to be coupled to an external surface of the shaft;
      a first sensor disposed on the distal end of the support member and for outputting a first signal indicative of current measured at a distal end of the active electrode; and
      a second sensor disposed on the proximal end of the support member and for outputting a second signal indicative of current measured at a proximal end of the active electrode,
      wherein a difference value of the first and second signal is indicative of leakage of current within the shaft.

11. The electrosurgical system of claim 10, further comprising a comparison circuit coupled to the first and second sensors for receiving the first and second signals and determining the difference value of the first and second signal.

12. The electrosurgical system of claim 11, further comprising a controller for controlling the output of electrosurgical energy and coupled to the comparison circuit for receiving the difference value, wherein if the difference value is greater than a predetermined threshold, the controller terminates the output of electrosurgical energy.

13. The electrosurgical system of claim 12, wherein the comparison circuit is disposed in the handpiece.

14. The electrosurgical system of claim 12, wherein the comparison circuit is disposed in the electrosurgical unit.

15. The electrosurgical system of claim 12, wherein the support member is a tube configured to be disposed around the shaft.

16. The electrosurgical system of claim 12, wherein the support member is a bar coupled to an external surface of the shaft.

17. The electrosurgical system of claim 12, wherein the support member includes a first clip for coupling the first sensor to the shaft and a second clip for coupling the second sensor to the shaft.

18. The electrosurgical system of claim 10, further comprising at least one conductor coupled to the first and second sensors configured to transmit the first and second signals to the electrosurgical generator.

19. The electrosurgical system of claim 10, further comprising a wireless transceiver coupled to the first and second sensors configured to transmit the first and second signals to the electrosurgical generator wirelessly.

20. An apparatus for use with an endoscopic applicator, the endoscopic applicator including a shaft having a proximal end and a distal end and an active electrode having a tip and being adapted for coupling to an electrosurgical generator and extending through the shaft for effecting at the tip thereof an electrosurgical procedure, the apparatus comprising:
   a tube-shaped support member configured to be removably disposed over a shaft of an endoscopic applicator;
   a first sensor supported by the support member and disposed adjacent the distal end of the shaft and for contactlessly sensing a first signal indicative of current measured at the distal end of the active electrode; and
   a second sensor supported by the support member and disposed adjacent the proximal end of the shaft and for contactlessly sensing a second signal indicative of current measured at the proximal end of the active electrode, wherein a difference value of the first and second signal is indicative of leakage of current within the shaft.

21. A cannula for use with an endoscopic applicator, the endoscopic applicator including a shaft having a proximal end and a distal end and an active electrode having a tip and being adapted for coupling to an electrosurgical generator and extending through the shaft for effecting at the tip thereof an electrosurgical procedure, the cannula comprising:
   a hub configured to receive the distal end of the endoscopic applicator;
   a tubular member connected to the hub configured to guide a shaft of the endoscopic applicator to a surgical site;
   a first sensor supported by the tubular member and disposed adjacent the distal end of the tubular member and for contactlessly sensing a first signal indicative of current measured at the distal end of the tubular member; and
   a second sensor supported by the tubular member and disposed adjacent the proximal end of the tubular member and for contactlessly sensing a second signal indicative of current measured at the proximal end of the tubular member,
   wherein a difference value of the first and second signal is indicative of leakage of current within the shaft.

22. The cannula of claim 21, further comprising a differential device disposed in the hub coupled to the first and second sensors for receiving the first and second signals and determining the difference value of the first and second signal.

23. The cannula of claim 21, further comprising a wireless transceiver disposed in the hub coupled to the first and second sensors configured to transmit the first and second signals to the electrosurgical generator wirelessly.

* * * * *